(12) United States Patent
Stanier et al.

(10) Patent No.: US 7,662,363 B2
(45) Date of Patent: Feb. 16, 2010

(54) AMORPHOUS SILICA

(75) Inventors: Peter W. Stanier, Sandbach (GB); Simon R. Stebbing, Warrington (GB)

(73) Assignee: PQ Silicas UK Limited, Barnsley, South Yorkshire (GB)

( * ) Notice: Subject to any disclaimer, the term of this patent is extended or adjusted under 35 U.S.C. 154(b) by 1110 days.

(21) Appl. No.: 10/499,683

(22) PCT Filed: Nov. 29, 2002

(86) PCT No.: PCT/GB02/05425

§ 371 (c)(1),
(2), (4) Date: Jan. 12, 2005

(87) PCT Pub. No.: WO03/055802

PCT Pub. Date: Jul. 10, 2003

(65) Prior Publication Data

US 2005/0129628 A1   Jun. 16, 2005

(30) Foreign Application Priority Data

Dec. 22, 2001   (GB) .................................. 0130907.9

(51) Int. Cl.
*A61K 8/18* (2006.01)
(52) U.S. Cl. ........................................ 424/49; 423/335
(58) Field of Classification Search .................... 424/49
See application file for complete search history.

(56) References Cited

U.S. PATENT DOCUMENTS

| | | | |
|---|---|---|---|
| 3,960,586 A | 6/1976 | Wason | |
| 4,122,161 A | 10/1978 | Wason | |
| 5,098,695 A | 3/1992 | Newton et al. | |
| 5,236,683 A | 8/1993 | Nakazawa et al. | |
| 5,366,645 A | 11/1994 | Sobottka | |
| 5,589,160 A | 12/1996 | Rice | |
| 5,603,920 A | 2/1997 | Rice | |
| 5,651,958 A | 7/1997 | Rice | |
| 5,658,553 A | 8/1997 | Rice | |
| 5,676,932 A | 10/1997 | Wason et al. | |
| 5,932,191 A | 8/1999 | Chevallier et al. | |
| 5,939,051 A | 8/1999 | Santalucia et al. | |
| 6,419,174 B1 * | 7/2002 | McGill et al. | ............ 427/249.1 |

FOREIGN PATENT DOCUMENTS

| | | |
|---|---|---|
| EP | 0236070 | 9/1897 |
| EP | 0227334 | 7/1987 |
| EP | 0236070 | 9/1987 |
| EP | 0341383 A2 | 2/1989 |
| EP | 0535943 | 4/1993 |
| EP | 0643015 A1 | 3/1995 |
| EP | 0666832 | 8/1995 |
| GB | 1482355 | 9/1974 |
| WO | 92/02454 A1 | 2/1992 |
| WO | 94/10087 | 5/1994 |
| WO | 95/14738 | 6/1995 |
| WO | WO 96/09809 | 4/1996 |
| WO | 97/02211 | 1/1997 |
| WO | WO 97/02211 | 1/1997 |
| WO | 99/51196 A1 | 10/1999 |

OTHER PUBLICATIONS

Stookey et al., "In vitro Removal of Stain with Dentifrices", J. Dent. Res. 61(11):1236-1239, Nov. 1982.
Wulknitz, P. "Cleaning Power and Abrasivity of European Toothpastes", Adv. Dent. Res. 11(4):576-579, Nov. 1997.

* cited by examiner

*Primary Examiner*—Frederick Krass
*Assistant Examiner*—Darryl C Sutton
(74) *Attorney, Agent, or Firm*—Buchanan Ingersoll & Rooney PC

(57) ABSTRACT

An amorphous silica suitable for use in a dental composition has a weight mean particle size in the range 3 to 15 µm with at least 90 per cent by weight of particles having a size below 20 µm, a Radioactive Dentine Abrasion (RDA) determined on an aqueous slurry of the silica powder of 100 to 220, a Pellicle Cleaning Ratio (PCR), when incorporated in a dental composition at 10 per cent by weight, greater than 85, the ratio of PCR to RDA being in the range 0.4:1 to less than 1:1 and having a Plastics Abrasion Value (PAV) in the range 11 to 19. A silica having the above properties is prepared by a precipitation route. The silica made available by the invention is also useful as an anti-blocking agent in plastics.

18 Claims, No Drawings

AMORPHOUS SILICA

CROSS REFERENCE TO RELATED APPLICATION

This application is the National Phase application of international Application No. PCT/GB02/05425, filed Nov. 29, 2002, which designates the United States and was published in English. This application, in its entirety, is incorporated herein by reference.

This invention relates to amorphous silica and particularly to amorphous silica suitable for use in dental compositions.

Amorphous silicas have been used as effective, compatible abrasives in dental compositions for a number of years. It is desirable that the silica should be efficient at cleaning the pellicle film from teeth but preferably should cause minimal damage to teeth. Recently, a number of silicas have been developed which provide good cleaning and relatively little abrasion, as measured by the standard test known as Radioactive Dentine Abrasion (RDA). Such silicas are described in, for example, WO 97/02211 and WO 96/09809. Generally, although these silicas have good cleaning properties in comparison with their abrasion properties, they possess a low RDA value. Consequently, in order to obtain a dentifrice having good cleaning performance, it is necessary to include relatively large quantifies of silica in the dentifrice (say 25 to 35 per cent by weight). The use of relatively large quantities of silica in a dentifrice is generally uneconomical and can be especially problematical for the Theological properties of the toothpaste, due to the space-filling effects of porous particles. It is therefore desirable to obtain a silica which has good cleaning performance at a relatively low loading (say 20 per cent or less) in a dentifrice.

According to this invention an amorphous silica suitable for use in a dental composition has a weight mean particle size in the range 3 to 15 µm with at least 90 per cent by weight of particles having a size below 20 µm, a Radioactive Dentine Abrasion (RDA) determined on an aqueous slurry of the silica powder of 100 to 220, a Pellicle Cleaning Ratio (PCR), when incorporated in a dental composition at 10 per cent by weight, greater than 85, the ratio of PCR to RDA being in the range 0.4:1 to less than 1:1 and having a Plastics Abrasion Value (PAV) in the range 11 to 19.

The silicas according to the invention possess a combination of properties distinctly different from known silicas suitable for dental compositions. They have a particularly effective ability to clean, which is demonstrated by relatively high PCR values exhibited at conventional RDA values in dentifrices containing a relatively small amount of the silica. Although the PCR to RDA ratio is less than 1, the RDA value is higher than known silicas with a higher PCR to RDA ratio and, compared to these products, a higher PCR is achievable with the same quantity of silica. In addition, the previously published relationship between RDA and PAV does not apply to these products. For example, EP 0 535 943 discloses a relationship between RDA and PAV in which an RDA value of 117 is equivalent to a PAV value of 16 and an RDA value of 195 is equivalent to a PAV value of 26. This model would predict that a PAV range of 11 to 19, as claimed herein, would necessarily imply an RDA range of about 80 to 140. The silicas according to the invention are also distinguishable from those disclosed in EP 0 535 943 and similar silicas disclosed in EP 0 666 832 by their superior cleaning performance. Silicas prepared according to the teachings of EP 0 535 943 or EP 0 666 832 have been shown to produce a PCR less than 85 when tested in a dental composition at 10 per cent by weight.

Plastics Abrasion Values are a measure of the amount of scratching produced on a surface by the silica and are therefore indicative of possible damage to teeth. The silicas according to this invention possess a moderate PAV but high PCR, which indicates good cleaning without excessive damage. In contrast, silicas produced according to EP 0 236 070 have a PAV in the range 23 to 35 (and RDA values between 150 and 300), but the cleaning properties are similar to those of silicas of the invention. However, the much higher PAV values of EP 0 236 070 are indicative of significantly greater scratching of tooth surfaces.

The amorphous silica according to the invention preferably has an oil absorption, using linseed oil, in the range 70 to 150 $cm^3/100$ g and, more preferably, the oil absorption is in the range 75 to 130 $cm^3/100$ g.

Also, the amorphous silica preferably has a BET surface area in the range 10 to 450 $m^2g^{-1}$, and, more preferably, the BET surface area is in the range 50 to 300 $m^2g^{-1}$.

The weight mean particle size of the silica according to the invention is determined using a Malvern Mastersizer® and a preferred material has a weight mean particle size in the range 5 to 10 µm. The particle size distribution and, hence, the proportion of particles having a size below any particular value can be determined by the same technique. For the amorphous silica of this invention, at least 90 per cent of the particles by weight preferably have a size below 17 µm.

In a particular embodiment of the invention, the weight mean particle size of the silica is in the range of 3 to 7 µm, with at least 90 per cent of the particles by weight having a size below 16 µm, preferably below 12 µm. Such silicas can be effectively used as a cleaning booster in dental compositions.

The Radioactive Dentine Abrasion (RDA) of the silicas of the invention has a value in the range 100 to 220. More commonly, the RDA has a value in the range 120 to 200 and, frequently, the RDA is above 140. Generally, silicas of the invention having a PAV above 15 will have an RDA above 120 and those having a PAV above 17 have an RDA above 140.

The PCR (measured in a dental composition at 10 per cent by weight) of the amorphous silica according to the invention is greater than 85, preferably greater than 90 and more preferably greater than 95. The PCR: RDA ratio is preferably in the range 0.5:1 to 0.9:1.

The amorphous silica according to the invention preferably has a pH value, measured on a 5 per cent by weight suspension, in the range 5 to 8, more preferably in the range 6 to 7.5.

The amount of water present on the amorphous silica suitable for use in a dental composition, as measured by the ignition loss at 1000° C., is usually up to 25 per cent by weight and preferably up to 15 per cent by weight Usually the ignition loss at 1000° C. is more than 4 per cent by weight Preferred amorphous silicas according to the invention have a Bound Water Content in the range 3.8 to 5.8 per cent by weight. Bound Water is determined by the difference between Moisture Loss measured at 105° C. and the Loss on Ignition at 1000° C.; it is characteristic of the underlying structure of the silica. Preferably, the Bound Water Content is in the range 4.0 to 5.5 per cent by weight and more preferably it is in the range 4.0 to 5.0 per cent by weight.

The Loose Bulk Density of preferred silicas according to the invention is in the range 200 to 400 $g/dm^3$.

The preferred silicas of the invention also have an intra-particle Pore Volume, determined by mercury intrusion, of less than 1.0 $cm^3/g$. Normally, the intra-particle Pore Volume is more than 0.1 $cm^3/g$.

In addition, it is preferred that the Mean Pore Diameter, which is a calculated parameter based on an assumption of cylindrical pores and derived from the following equation:

$$\text{Mean Pore Diameter (in nm)} = \frac{4000 \times \text{Pore Volume (in cm}^3\text{g}^{-1})}{\text{Surface Area (in m}^2\text{g}^{-1})}$$

is in the range 5 to 45 nm. More preferred silicas of the invention have a Mean Pore Diameter in the range 10 to 30 nm and particularly preferred silicas have a Mean Pore Diameter in the range 12 to 25 nm.

A second aspect of the invention comprises a dental composition comprising an amorphous silica having a weight mean particle size in the range 3 to 15 µm with at least 90 per cent by weight of particles having a size below 20 µm, a Radioactive Dentine Abrasion (RDA) determined on an aqueous slurry of the silica powder of 100 to 220, a Pellicle Cleaning Ratio (PCR) when incorporated in a dental composition at 10 per cent by weight, greater than 85, the ratio of PCR to RDA being in the range 0.4:1 to less than 1:1 and having a Plastics Abrasion Value (PAV) in the range 11 to 19 and an orally acceptable carrier.

The dental composition can be in any form suitable as a dental composition, such as a paste, gel, cream or liquid.

Generally, the amount of amorphous silica present in this dental composition is in the range 0.1 to 25 per cent by weight but the amount present depends to some extent on the precise function of the silica. When used in the conventional manner, as the principal abrasive, the amount present is preferably in the range 0.5 to 25 per cent by weight, more preferably in the range 1 to 20 per cent by weight and the amorphous silicas of this invention are especially useful when used in a dental composition in an amount in the range 1 to 15 per cent by weight, since such dental compositions provide good cleaning and have acceptable abrasion properties. When the silica of the invention is used as a cleaning booster having a relatively small particle size, as described hereinbefore, it is preferably present in an amount in the range 0.1 to 6 per cent by weight.

A particularly preferred dental composition according to this invention comprises a mixture of a first amorphous silica, being an amorphous silica according to the invention, a second amorphous silica having a lower RDA value than said first amorphous silica and an orally acceptable carrier. Preferably, the second amorphous silica has an RDA in the range 40 to 130 and most preferably the RDA of the second silica is in the range 70 to 110. An example of a suitable second silica is the product sold under the trade name Sorbosil AC35 by INEOS Silicas Limited, Warrington, UK, which has a typical silica RDA of 105. Such compositions have surprisingly been found to give better cleaning than compositions containing the first silica alone but the RDA of the composition is similar to that of a composition containing only the first silica.

When the dental composition comprises such a mixture of silicas, the first amorphous silica is preferably present in an amount in the range 1 to 15 per cent by weight of the composition and the second silica is preferably present in an amount in the range 4 to 20 per cent by weight of said composition. More preferably, the second silica is present in an amount in the range 5 to 15 per cent by weight of said composition.

An alternative dental composition according to the invention contains a first silica which is an amorphous silica according to this invention and having an average particle size in the range 3 to 7 µm with at least 90 per cent of the particles by weight having a particle size below 16 µm (booster silica) and a second silica (principal silica). In this composition, the principal silica can be a silica according to the invention having an average particle size larger than that of the booster silica. Alternatively, the booster silica can be used in conjunction with any conventional silica which is useful in dental compositions. Generally, in such compositions, the booster silica is present in an amount in the range 0.1 to 6 per cent by weight of the dental composition and preferably in the range 0.5 to 4 per cent by weight of the composition and the principal silica is present in an amount in the range 4 to 25 per cent by weight of the dental composition. Preferably, the principal silica is present in the range 7 to 19 per cent by weight of the dental composition.

Water is usually present as a component of the dental compositions of the invention normally in an amount of from about 1 to about 90 per cent by weight, preferably from about 10 to about 60 per cent, more preferably from about 15 to about 50 per cent by weight For clear pastes the water content is preferably from about 1 to about 20 per cent by weight and more preferably is in the range 5 to 15 per cent by weight.

For the preparation of a clear (or transparent) paste, a suitable silica according to the invention shows a maximum transparency with Light Transmission of at least 70 per cent at a refractive index in the range 1.435 to 1.445.

When the dental composition is a toothpaste or cream it contains at least one humectant, for example a polyol such as glycerol, sorbitol syrup, polyethylene glycol, lactitol, xylitol or hydrogenated corn syrup. The total amount of humectant is preferably in the range about 10 to about 85 per cent by weight of the composition.

The dental composition of the invention may include one or more surfactants, preferably selected from anionic, non-ionic, amphoteric and zwitterionic surfactants, and mixtures thereof, all being suitable for oral use. The amount of surfactant present in the composition of the invention is typically from about 0.1 to about 3 per cent by weight (based upon 100 per cent activity).

Suitable anionic surfactants may include soaps, alkyl sulphates, alkyl ether sulphates, alkaryl sulphonates, alkanoyl isethionates, alkanoyl taurates, alkyl succinates, alkyl sulphosuccinates, N-alkoyl sarcosinates, alkyl phosphates, alkyl ether phosphates, alkyl ether carboxylates and alpha-olefin sulphonates, especially their sodium, magnesium, ammonium and mono-, di- and tri-ethanolamine salts. The alkyl and acyl groups generally contain from 8 to 18 carbon atoms and may be saturated. The alkyl ether sulphates, alkyl ether phosphates and alkyl ether carboxylates may contain from one to 10 ethylene oxide or propylene oxide units per molecule, and preferably 2 to 3 ethylene oxide units per molecule. Examples of preferred anionic surfactants include sodium lauryl sulphate, sodium dodecylbenzene sulphonate, sodium lauroyl sarcosinate and sodium coconut monoglyceride sulphonate.

Non-ionic surfactants which may be suitable for use in the dental composition of the invention include sorbitan and polyglycerol esters of fatty acids, as well as ethylene oxide/propylene oxide block copolymers.

Suitable amphoteric surfactants include betaines such as cocamidopropyl betaine and sulphobetaines.

The dental compositions of the present invention preferably include one or more thickening agents and/or suspending agents in order to give the composition the desired physical properties (e.g. whether a paste, cream or a liquid) and in order that the amorphous silica of the invention remains stably dispersed throughout the composition.

A particularly preferred means for thickening the dental compositions of the invention is by the inclusion of a thickening silica in conjuncton with a polymer suspending or thickening agent. Suitable well-known polymer suspending or thickening agents, which may be used alone or in conjunction with a thickening silica, include polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof, heteropolysaccharide gums such as xanthan and guar gums, and cellulose derivatives such as sodium carboxymethyl cellulose. Particularly suitable suspending or thickening agents are xanthan gum and sodium carboxymethyl cellulose. These thickeners (which may be used singly or as mixtures of two or more of the above materials) may be present in the composition in a total amount of from about 0.1 to about 5 per cent by weight. When used with silica thickening agents they are preferably present in an amount in the range 0.1 to 5.0 per cent by weight. Silica thickening agents, such as the silica sold under the trade name Sorbosil TC15 by INEOS Silicas Limited, Warrington, UK, when present, comprise from about 0.1 to about 15 per cent by weight, preferably about 1 to about 10 per cent by weight of the composition.

Frequently, the dental compositions of the invention contain chelating agents such as tartaric acid, citric acid, alkali metal citrates, soluble pyrophosphates, such as alkali metal pyrophosphates, and polymeric polycarboxylates.

One or more other components that are conventionally found in a dental composition may be present in the dental composition and include the following; flavouring substances such as peppermint, spearmint; artificial sweeteners; perfume or breath freshening substances; pearlescing agents; peroxy compounds such as hydrogen peroxide or peracetc acid; opacifiers; pigments and colourings; preservatives; moisturising agents; fluoride-containing compounds; anti-caries and anti-plaque agents; anti-tartar agents; anti-hypersensitvity agents; therapeutic agents such as zinc citrate, Triclosan (ex Ciba Geigy); proteins; enzymes; salts; baking soda and pH adjusting agents.

Dental compositions in accordance with the invention may be made by conventional methods for preparing such compositions. Pastes and creams may be prepared by conventional techniques, for example, using high shear mixing systems under vacuum.

Preferably, the amorphous silica according to the invention is a precipitated silica and a third aspect of the invention comprises a process for the preparation of an amorphous silica comprising the steps of:

(a) introducing an amount of an aqueous solution of alkali metal silicate, having an $SiO_2:M_2O$ molar ratio, where M is an alkali metal, in the range from 2.0:1 to 3.4:1 and a first amount of mineral acid into an aqueous reaction mixture whilst applying high shear from an in-line mixer to the reaction mixture, the alkali metal silicate solution and the mineral acid being supplied at a rate which ensures that the pH of the reaction mixture is held substantially constant at a value in the range from about 9 to about 11, the concentration of silica after the addition of the first amount of mineral acid being from about 5.5 to about 7.5 per cent by weight of the reaction mixture, the temperature of the reaction mixture during introduction of the alkali metal silicate and the mineral acid being in the range of about 60° C. to about 80° C. and the period over which the alkali metal silicate and the mineral acid are introduced being between 40 and 80 minutes, in the presence of a water soluble electrolyte, wherein the electrolyte is present in an amount such that the weight ratio of electrolyte to silica is from about 0.1:1 to 0.25:1, (b) increasing the temperature of the reaction mixture to a temperature in the range 90 to 100° C., (c) maintaining the reaction mixture at this temperature for a period in the range 5 to 30 minutes, (d) adding to the reaction mixture a second amount of mineral acid over a period in the range 5 to 20 minutes, said second amount being sufficient to adjust the pH of the reaction mixture to a value in the range 3 to 5, (e) filtering the silica thus produced from the reaction mixture and washing and flash drying the silica, and (f) comminuting the dried silica to the desired particle size distribution.

Optionally, an ageing step can be introduced during the addition of the second amount of mineral acid [Step(d)] wherein the acid addition is paused at a pH in the range 5 to 6 and the reaction mixture is maintained for a period in the range 5 to 30 minutes at a pH in the range 5 to 6 and a temperature in the range 90° C. and 100° C., after which the second addition of mineral acid is continued.

In the process according to the invention, the alkali metal silicate can be any alkali metal silicate but the readily available sodium silicate is usually preferred. The sodium silicate preferably has an $SiO_2: Na_2O$ weight ratio in the range 3.2:1 to 3.4:1 and a concentration, expressed as $SiO_2$, in the range 14 to 20 per cent by weight The preferred mineral acid for use in the process of the invention is sulphuric acid at a concentration in the range 15 to 20 per cent by weight It is important that the reaction mixture is subjected to high shear during the introduction of silicate and acid. One suitable means of applying this shear is to pass the mixture through a Silverson in-line mixer throughout the entire reaction period, the Silverson mixer being internally configured with a square hole high shear screen or disintegrating head, as defined by the manufacturer.

A number of compounds are suitable as water soluble electrolytes. Commonly, the electrolyte is a salt of an alkali metal, such as a chloride or sulphate and preferred electrolytes are sodium chloride and sodium sulphate, with sodium chloride being the most preferred.

After the silica formed in the process of the invention is separated from the reaction mixture it is washed to remove salts. Typically, it is washed until any residual salt is below 2 per cent by weight, based on dry silica.

The dry silica is comminuted to an appropriate particle size distribution. The comminution can be carried out using a mill such as a rotating beater mill with air classifier. Preferably, when a small mean particle size is desired, as with the silica described hereinbefore as booster silica, the comminution is carried out using a fluid energy mill or microniser with integral air classifier.

Silica having the aforementioned properties or made according to the process described above has also been found to be useful as an anti-blocking agent in polymer films. The silica is incorporated into polymeric films and its presence helps to facilitate separation of films from one another. This is known as the "anti-blocking" effect Accordingly, a fourth aspect of the invention comprises the use of amorphous silica having a weight mean particle size in the range 3 to 15 μm with at least 90 per cent by weight of particles having a size below 20 μm, a Radioactive Dentine Abrasion (RDA) determined on an aqueous slurry of the silica powder of 100 to 220, a Pellicle Cleaning Ratio (PCR), when incorporated in a dental composition at 10 per cent by weight, greater than 85, the ratio of PCR to RDA being in the range 0.4:1 to less than 1:1 and having a Plastics Abrasion Value (PAV) in the range 11 to 19 as an anti-blocking agent in a polymer composition.

The parameters which characterise the silica of the invention are generally associated with the characterisation of silicas suitable for use in dental compositions. However, it is believed that these parameters describe the characteristic structure of the silica and it has been surprisingly discovered that silica characterised by these parameters is also extremely useful as an anti-blocking agent in polymer films.

Silicas useful in the fourth aspect of this invention preferably have a Bound Water Content in the range 3.8 to 5.8 per cent by weight. They also preferably have a Loose Bulk Density in the range 200 to 400 g/dm$^3$. In addition, it is preferred that they have a Mean Pore Diameter in the range 5 to 45 nm.

The process of the invention provides a method of producing an amorphous silica which can be characterised by a weight mean particle size in the range 3 to 15 μm with at least 90 per cent by weight of particles having a size below 20 μm, a Bound Water Content in the range 3.8 to 5.8 per cent by weight, a Loose Bulk Density in the range 200 to 400 g/dm$^3$ and a Mean Pore Diameter in the range 5 to 45 nm and this silica is useful as an anti-blocking agent in plastics films. Consequently, a fifth aspect of the invention comprises the use of an amorphous silica having a weight mean particle size in the range 3 to 15 μm with at least 90 per cent by weight of particles having a size below 20 μm, a Bound Water Content in the range 3.8 to 5.8 per cent by weight, a Loose Bulk Density in the range 200 to 400 g/dm$^3$ and a Mean Pore Diameter in the range 5 to 45 nm as an anti-blocking agent for a polymer composition.

The preparative route described above for the silica is a "precipitation" route and the silica made thus therefore possesses the good optical properties associated with such silica. These properties are generally superior to those of silica gels, which are frequently used as anti-blocking agents. The anti-blocking properties of the silica are also extremely good. Incorporation of the silica into polyolefin films gives similar performance (reduction in film blocking force) at equal loading to those silica gels commonly used as anti-blocking agents. In addition, the structure of the silica of the invention minimises slip agent adsorption allowing for more effective use of such additives.

The silica according to the invention is especially useful as an anti-blocking agent in olefin polymers such as polyethylene and, particularly, polypropylene.

The amount incorporated into the polymer is usually in the range 0.05 to 0.5 per cent by weight with respect to the polymer and preferably in the range 0.10 to 0.40 per cent by weight with respect to the polymer.

Silicas of the invention which are useful as anti-blocking agents preferably have a weight mean particle size in the range of 3 to 10 ;m, with at least 90 per cent of the particles by weight having a size below 17 μm. More preferably such silicas have a weight mean particle size in the range 3 to 7 μm with at least 90 per cent of the particles by weight having a size below 16 gm, preferably below 12 μm.

In the use of silicas as anti-blocking agents according to the invention, it is preferred that the silicas have a Bound Water Content in the range 4.0 to 5.5 per cent by weight, more preferably in the range 4.0 to 5.0 per cent by weight. It is also preferred that the silicas used as anti-blocking agents according to the invention have a Mean Pore Diameter in the range 10 to 30 nm and it is more preferred that they have a Mean Pore Diameter in the range 12 to 25 nm. Generally, silicas used as anti-blocking agents according to the invention have an intra-particle Pore Volume, determined by mercury intrusion, in the range 0.1 to 1.0 cm$^3$g$^{-1}$.

Usually silicas having a relatively low moisture loss are preferred as anti-blocking agents and it is preferable that silicas used as anti-blocking agents according to the invention have a moisture loss at 105° C. of up to 5.0 per cent by weight. Silicas with a moisture loss of up to 3.0 per cent by weight at 105° C. are more preferred.

The silicas of the invention can be combined with slip agents and the combinations used as additives for polymers to provide combined anti-blocking and slip agents. The slip agents used in such combinations can be any conventional slip agents such as amides of unsaturated acids, particularly $C_{18}$ to $C_{22}$ unsaturated fatty acids and especially oleic acid amide and erucic acid amide. Preferred combined anti-blocking and slip agents comprise from 20 to 80 per cent by weight of an amide of one or more $C_{18}$ to $C_{22}$ unsaturated fatty acids and 20 to 80 per cent by weight of a silica according to this invention.

When used as anti-blocking agents, the silicas of the invention are mixed with a polymer using any suitable means of preparing such mixtures. For example, the silica, polymer and any other components of the final composition, such as slip agents, pigments, stabilisers and antioxidants, are combined in a single or twin screw extruder or an internal ("Banbury"-type) mixer until a homogeneous composition is produced. Films can be prepared from this composition by standard casting or blown film extrusion techniques. Alternatively, a master batch which contains a relatively high concentration of the silica of the invention and, optionally, other ingredients such as slip agents can be prepared. The master batch is subsequently mixed with virgin polymer to produce a final composition in which the silica of this invention is homogeneously distributed. A master batch generally contains from 1 to 50 weight per cent of the silica or of a combined anti-blocking and slip agent as described hereinbefore.

The amorphous silicas according to the invention are characterised by the use of the following tests.

Oil Absorption

The oil absorption is determined by the ASTM spatula rub-out method (American Society of Test Material Standards D 281). The test is based on the principle of mixing linseed oil with the silica by rubbing with a spatula on a smooth surface until a stiff puttylike paste is formed which will not break or separate when it is cut with a spatula. The oil absorption is then calculated from the volume of oil (V cm$^3$) used to achieve this condition and the weight, W, in grams, of silica by means of the equation:

Oil absorption=($V$×100)/$W$, i.e. expressed in terms of cm$^3$ oil/100 g silica.

BET Surface Area

Surface area the silica is measured using standard nitrogen adsorption methods of Brunauer, Emmett and Teller (BET) using a multi-point method with an ASAP 2400 apparatus supplied by Micromeritics of USA. The method is consistent with the paper by S. Brunauer, P. H. Emmett and E. Teller, J. Am. Chem. Soc., 60, 309 (1938). Samples are outgassed under vacuum at 270° C. for 1 hour before measurement at about −196° C.

Weight Mean Particle Size and Particle Size Distribution by Malvern Mastersizer®

The weight mean particle size of the silica is determined using a Malvem Mastersizer® model S, with a 300 RF lens and MS17 sample presentation unit. This instrument, made by Malvern Instruments, Malvem, Worcestershire, uses the principle of Fraunhofer diffraction, utilising a low power He/Ne laser. Before measurement, the sample is dispersed ultrasonically in water for 5 minutes to form an aqueous suspension. The Malvem Mastersizer® measures the weight particle size distribution of the silica. The weight mean particle size ($d_{50}$) or 50 percentile and the percentage of material below any specified size (in particular, for this invention, 20 µm, 17 µm, 16 µm, 12 µm or 10 µm) are easily obtained from the data generated by the instrument.

Radioactive Dentine Abrasion Test (RDA)

The procedure follows the method for assessment of dentifrice abrasivity recommended by the American Dental Association (Journal of Dental Research 55(4) 563, 1976). In this procedure, extracted human teeth are irradiated with a neutron flux and subjected to a standard brushing regime.

The radioactive phosphorous 32 removed from the dentin in the roots is used as the index of the abrasion of the dentifrice tested. A reference slurry containing 10 g of calcium pyrophosphate in 50 cm³ of 0.5% aqueous solution of sodium carboxymethyl cellulose is also measured and the RDA of this mixture is arbitrarily taken as 100. The precipitated silica to be tested is prepared as a suspension of 6.25 g in 50 cm³ of 0.5% aqueous solution of sodium carboxymethyl cellulose and submitted to the same brushing regime.

Plastics Abrasion Value (PAV)

This test is based upon a toothbrush head brushing a Perspex® plate in contact with a suspension of the silica in a sorbitouglycerol mixture. Perspex® has a similar hardness to dentine. Therefore, a substance which produces scratches on Perspex® is likely to produce a similar amount of scratching on dentine. Normally the slurry concentration is as follows:

| | |
|---|---|
| Silica | 2.5 g |
| Glycerol | 10.0 g |
| Sorbitol Syrup* | 23.0 g |

*Syrup contains 70% sorbitol/30% water

All components are weighed into a beaker and dispersed for 2 minutes at 1500 rpm using a simple stirrer. A 110 mm×55 mm×3 mm sheet of standard PERSPEX clear cast acrylic sheet, grade 000, manufactured by INEOS Acrylics Limited, is used for the test.

The test is carried out using a modified Wet Scrub Abrasion Tester produced by Sheen Instruments.

The modification is to change the holder so that a toothbrush can be used in place of a paintbrush. In addition, a weight of 400 g is attached to the brush assembly, which weighs 145 g, to force the brush onto the PERSPEX sheet. The toothbrush has a multi-tufted, flat trim nylon head with round ended filaments and medium texture, for example, one sold as Professional Mentadent P gum health design, manufactured by Unilever PLC under the Gibbs trade name.

A galvanometer is calibrated using a 45° Plaspec gloss head detector and a standard (50% gloss) reflecting plate. The galvanometer reading is adjusted to a value of 50 under these conditions. The reading of the fresh PERSPEX sheet is then carried out using the same reflectance arrangement. The fresh piece of PERSPEX sheet is then fitted into a holder. 2 cm³ of the dispersed silica, sufficient to lubricate fully the brushing stroke, is placed on the sheet and the brush head is lowered onto the sheet. The machine is switched on and the sheet is subjected to 300 strokes of the weighted brush head. The sheet is removed from the holder and all the suspension is washed off. It is then dried and its gloss value is determined again. The abrasion value is the difference between the unabraded gloss value and the gloss value after abrasion. This test procedure, when applied to known abrasives, gave the following typical values.

| | PAV |
|---|---|
| Calcium carbonate (15 µm) | 32 |
| Silica xerogel (10 µm) prepared according to GB 1 262 292 | 25 |
| Alumina trihydrate (Gibbsite) (15 µm) | 16 |
| Calcium pyrophosphate (10 µm) | 14 |
| Dicalcium phosphate dihydrate (15 µm) | 7 |

Pellicle Cleaning Ratio (PCR)

The PCR is measured using the test described by G. T. Stookey et al. in Journal of Dental Research, November 1982, pages 1236 to 1239. Full details are available in this paper. Bovine permanent central incisors are cut to obtain specimens approximately 10 mm² which are embedded in a methacrylate resin. The enamel surfaces are smoothed and polished on a lapidary wheel and lightly etched by a 60 second in immersion in 0.12 N (1%) hydrochloric acid followed by a 30 second immersion in super-saturated sodium carbonate and a final etch with 1% phytic acid for 60 seconds, after which they are rinsed with deionised water. The specimens are then rotated at 2 rpm and 37° C. for 4 days through a staining broth prepared by dissolving 2.7 g finely-ground instant coffee, 2.7 g finely-ground instant tea and 2.0 g finely ground gastric mucin in 800 cm³ sterilised trypticase soy broth. 26 cm³ of a 24-hour Sarcina lutea turtox culture were also added to the staining broth with the broth being replaced twice daily. The samples are rotated through the broth and air. The samples are then removed from the apparatus, rinsed well, allowed to air dry and stored under refrigeration until used. The amount of stain is graded on an arbitrary scale by examination at 25X under a binocular microscope. Using the baseline scores thus obtained, the specimens are divided into groups of 8 specimens having equivalent average baseline scores, and mounted on a V-8 mechanical cross-brushing machine equipped with soft filament nylon toothbrushes adjusted to 150 g tension upon the enamel surface. The dentifrice, containing the test silica at 10 per cent by weight loading, is tested as a slurry consisting of 25 g dentifrice mixed with 40 cm³ deionised water and the specimens are brushed for 800 double strokes. After brushing, the specimens are rinsed, blofted dry and graded again. The difference between pre- and post-test scores is considered to represent the ability of the test dentifrice to remove the stain. A standard lot of calcium pyrophosphate is assessed as a slurry and allotted the arbitrary cleaning value of 100.

The cleaning scores of the test materials are expressed as a ratio:

$$\frac{\text{Mean decrement for test material}}{\text{Mean decrement for reference material}} \times 100 = \text{Pellicle Cleaning Ratio}$$

pH

This measurement is carried out on a 5 weight per cent suspension of the silica in boiled demineralised water ($CO_2$ free).

Ignition Loss at 1000° C.

Ignition loss is determined by the loss in weight of a silica when ignited in a furnace at 1000° C. to constant weight.

Moisture Loss at 105° C.

Moisture loss is determined by the loss in weight of a silica when heated in an oven at 105° C. to constant weight.

Loose Bulk Density

Loose bulk density is determined by weighing approximately 180 cm³ of silica into a dry 250 cm³ measuring cylinder, inverting the cylinder ten times to remove air pockets and reading the final settled volume.

$$\text{Loose Bulk Density (in g/dm}^3) = \frac{\text{Weight (g)}}{\text{Volume (dm}^3)}$$

Tapped Bulk Density

The same procedure is adopted as for Loose Bulk Density except that the measuring cylinder is subjected to 200 taps in a mechanical tapper, manufactured by Quantachrome Corporation (Dual Autotap model No. DA-2) with a drop height of 4 mm. A reading is taken of the final settled volume and used to calculate the Tapped Bulk Density using the same equation as is used for Loose Bulk Density.

Sulphate and Chloride Contents

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

Iron Content

This is determined from solution by first removing silica as silicon tetrafluoride, utlising hydrofluoric acid, and dissolving any remaining residue in nitric acid. The total Fe in the silica is then determined by induction coupled plasma atomic emission spectroscopy, using standard Fe solutions in accordance with the equipment manufacturer's instructions.

Mercury Pore Volume

Mercury Pore Volume is determined by standard mercury intrusion procedures using a Micromerifics Autopore 9220 mercury porosimeter. The pore radius is calculated from the Washburn equation using values of surface tension for mercury of 485 mN/m and a contact angle of 140°.

Prior-to measurement the sample is outgassed at room temperature to a pressure of 6.7 Pa. Mercury Pore Volume can be split into two components: intra- and inter-particle porosity. The inter-particle porosity is a measure of the packing of the aggregated structure and is influenced by particle size. The intra-particle porosity, which is used to characterise the silicas of this invention, is a measure of the porosity of the fundamental particles and is determined by the wet processing conditions.

The Mercury Pore Volume recorded is that occurring over the range of calculated pore diameters of 0.05 to 1.0 micron to represent the true intra-particle porosity of the silica from the mercury intrusion curve, i.e. the porosity of the voids within the particles.

Light Transmission

The sample of silica is dispersed in a range of Sorbitol syrup (70% Sorbitol)/water mixtures at 4% by 20 weight concentration. After de-aeration, usually 1 hour, the transmission of the dispersions is determined using a spectrophotometer at 589 nm; water being used as blank. The refractive index of each dispersion is also measured using an Abbe refractometer.

A graphical representation of transmission plotted against refractive index allows the range of refractive indices over which the transmission exceeds 70% to be determined. The maximum transmission of the sample and the apparent refractive index of silica at which this is obtained can also be estimated from this graph.

The invention is illustrated by the following non-limiting examples.

EXAMPLES

A heated, baffled, stirred reaction vessel configured with an external shear device was used for the silicate/acid reaction.

Mixing is an important feature in the reaction of silicate and sulphuric acid. Consequently fixed specifications, as listed in Chemineer Inc. Chem Eng. 26 April 1976 pages 102-110, have been used to design the baffled, heated, stirred reaction vessel. Whilst the turbine design is optional to the mixing geometry, a 6-bladed 30° pitched bladed unit has been chosen for the examples in order to ensure maximum mixing effectiveness with minimum shear. Shear was supplied to the reaction mixture by circulating the contents of the reaction vessel through an external high shear mixer (Silverson), containing a square hole high shear screen, throughout the simultaneous addition of silicate and acid, the energy input being commensurate with the volume flow and number of recirculations required as specified by the manufacturer to give an energy input of at least 0.36 MJ/kg $SiO_2$.

The solutions used in the process were as follows:
a) A sodium silicate solution with a specific gravity of 1.2, an $SiO_2$: $Na_2O$ weight ratio in the range 3.24:1 to 3.29:1 and an $SiO_2$ concentration of 16.5 per cent by weight.
b) A sulphuric acid solution of specific gravity 1.12 (17.5 per cent solution by weight).

The following procedure was adopted in the preparation of the precipitated silicas. Values of reactant concentrations, volumes, temperatures and ageing steps are given in Table 1.

(A) dm³ of water were placed in the vessel with (B) dm³ of sodium silicate solution and (C) dm³ of 25% by weight aqueous sodium chloride solution. This mixture was then stirred and heated to (D)° C. (E) dm³ of sodium silicate and (F) dm³ of sulphuric acid were then simultaneously added over 60 minutes at (D)° C. The flow rates of the silicate and acid solutions were uniform throughout the addition period to ensure that a constant pH was maintained in the vessel.

The resultant slurry was aged for (G) minutes at (H)° C.

A further amount of sulphuric acid solution was then added over a period of (I) minutes until the pH was reduced to 5. The slurry was then adjusted to the end of batch pH (J).

The final slurry was then filtered and washed with water to reduce the excess salts present to less than 2 per cent by weight, based on dry silica. After washing, the filter cake in each example was flash dried to remove the water rapidly from the silica so that the structure was maintained, and the dry silica was comminuted to the desired particle size range.

The precipitated silicas obtained had the properties listed in Table 2, expressed on a dry weight basis.

TABLE 1

|  | Example 1 | Example 2 |
|---|---|---|
| Vessel Capacity ($dm^3$) | 300 | 300 |
| Water Volume (A) ($dm^3$) | 133.9 | 143.2 |
| Silicate ratio $SiO_2$:$Na_2O$ by wt. | 3.29 | 3.24 |
| $SiO_2$ Concentration in Silicate (percent by weight) | 16.5 | 16.5 |
| Silicate volume (B) ($dm^3$) | 1.1 | 1.1 |
| Sodium chloride solution volume (C) ($dm^3$) | 12.0 | 11.9 |
| Silicate volume (E) ($dm^3$) | 106.9 | 107.8 |
| Acid density (g/$cm^3$) | 1.12 | 1.12 |
| Acid volume (F) ($dm^3$) | 46.2 | 36.1 |
| Temperature (D) (° C.) | 80 | 65 |
| Age Temperature (H) (° C.) | 94 | 94 |
| Second acid addition time (I) (mins.) | 7 | 7 |
| Age time (G) (mins.) | 15 | 15 |
| End of batch pH (J) | 4 | 4 |

TABLE 2

| TEST | Example 1 | Example 2 |
|---|---|---|
| Oil Absorption ($cm^3$/100 g) | 79 | 130 |
| BET Surface Area ($m^2$/g) | 64 | 252 |
| Weight Mean Particle Size (μm) | 6.8 | 7.7 |
| Ninetieth Percentile Particle Size by Weight (μm) | 15.0 | 15.3 |
| RDA of Silica | 200 | 133 |
| Perspex Abrasion Value | 17 | 14 |
| Pellicle Cleaning Ratio at 20 wt. % loading in Formulation B | 119 | 96 |
| Pellicle Cleaning Ratio at 10 wt. % loading in Formulation A | 96 | 93 |
| pH of a 5 weight percent aqueous slurry | 7.5 | 7.1 |
| Ignition loss at 1000° C. | 7.8 | 10.5 |
| Moisture Loss at 105° C. (%) | 3.6 | 5.7 |
| Bound Water (%) | 4.2 | 4.8 |
| Loose Bulk Density (g/$dm^3$) | 363 | 253 |
| Tapped Bulk Density (g/$dm^3$) | 421 | 304 |
| Mercury Pore Volume ($cm^3$ $g^{-1}$) | 0.34 | 0.83 |
| Mean Pore Diameter (nm) | 21 | 13 |
| Maximum percent Transmission | 70 | 85 |
| at a Refractive Index of | 1.440 | 1.438 |
| $SO_4^{2-}$ (%) | 0.17 | 0.21 |
| $Cl^-$ (%) | 0.07 | 0.05 |
| Fe (ppm) | 250 | 300 |

Formulations A and B of the dentifrices used to measure the Pellicle Cleaning Ratio were as shown in Table 3 below.

TABLE 3

| COMPONENT | FORMULATION A (% by weight) | FORMULATION B (% by weight) |
|---|---|---|
| water | 27.6 | 27.6 |
| sorbitol | 30.8 | 25.8 |
| silica abrasive of the invention | 10.0 | 20.0 |
| silica thickener, Sorbosil TC 15 | 11.0 | 6.0 |
| glycerine | 9.5 | 9.5 |
| Polyethylene glycol (PEG 600) | 3.0 | 3.0 |
| tetrapotassium pyrophosphate | 2.0 | 2.0 |
| sodium lauryl sulphate | 2.0 | 2.0 |
| aqueous sodium hydroxide (50 wt %) | 1.0 | 1.0 |
| flavour | 1.0 | 1.0 |
| sodium monofluorophosphate | 0.8 | 0.8 |
| sodium carboxymethyl cellulose | 0.6 | 0.6 |
| titanium dioxide | 0.5 | 0.5 |
| saccharin | 0.2 | 0.2 |

Sorbosil TC15 is a thickening silica available from INEOS Silicas Limited, Warrington, UK.

Example 3

A masterbatch was prepared by combining 2.0 parts by weight of silica as prepared in Example 1 above with 98.0 parts by weight of polypropylene [Masplene MAS5402 (ASTM Melt Flow Index, 230° C., 2.16 kg=12 g/10 min) manufactured by PT Polytama Propindo, Jakarta, Indonesia] at a melt temperature of 220 to 240° C. using an APV MP2030-25 XLT Twin-screw compounding extruder fitted with a 5 mm strand die and pelletiser. The resulting masterbatch was dry mixed with virgin polymer to produce a composition which contained 0.35 parts by weight of silica and the resulting mixture was blown into films of nominal single-ply thickness 25±5 μm using a Kween B (Taiwan) PP 45/500 Blown PP Film Unit. The properties of the films produced were measured as follows.

Induced Blocking Force

Induced blocking force of the prepared film samples was measured according to 'Method B' of BS2782: Part 8: Method 825A:1996 and ISO 11502:1995. Blocking conditions used to induce blocking in specimens prepared from the film samples were adjusted from those specified in Section 5.42 of the method to allow for the type of film manufacturing process used and likely service of the prepared film. Weights of mass 5.7 kg were therefore placed on each assembly (method specifies 2.3 kg) and the assemblies were heated in an oven for 24 hrs at 60° C.±2° C., (method specifies 3 hrs at 50° C.±2° C.). The induced blocking force of specimens prepared under such conditions was measured using a Testometric Micro 350 Universal Materials Testing Instrument fitted with a 5 kgf (50N) load cell. The maximum force necessary to separate the film plies was recorded for each sample specimen and results (5 per sample) averaged for each specimen set to give the induced blocking force (N) for that particular film sample.

Static and Dynamic Coefficients of Friction

Static and dynamic coefficients of friction for the prepared film samples were measured according to BS2782: Part 8: Method 824A:1996 and ISO 8295:1995 using a Ray-Ran Polytest Advanced Static and Dynamic Coefficient of Friction Tester. The method places the surfaces,(in this case the two plies of the blown film sample) in plane contact with each other under uniform contact pressure. The force needed to displace the surfaces relative to each other is recorded and can be resolved into static and dynamic components giving measurements of the static and dynamic coefficients of friction.

Haze and Luminous Transmittance

Haze and luminous transmittance levels for the prepared film samples were measured according to ASTM D1003-92 using a BYK Gardner Haze-Gard Plus Instrument.

The results are shown in Table 4 below.

TABLE 4

|  | Silica of Invention | Reference Material |
|---|---|---|
| % Decrease in Induced Blocking Force, N | 52.1 | 64.7 |
| % Decrease in Static Coefficient of Friction, μ | 74.2 | 83.3 |
| % Decrease in Dynamic Coefficient of Friction, μ | 51.7 | 40.4 |

TABLE 4-continued

|  | Silica of Invention | Reference Material |
|---|---|---|
| % Increase in Haze | 1.5 | 2.6 |
| % Increase in Luminous Transmittance | 0.02 | 0.02 |

*Reference material was an anti-blocking silica sold under the trade name SYLOBLOC 45 by Grace-Davison and available from Grace GmbH, Worms, Germany.
Decrease or increase data shown relative to polymer films prepared from virgin polymer (no anti-blocking agent added).

The invention claimed is:

1. An amorphous silica suitable for use in a dental composition having a weight mean particle size in the range 3 to 15 μm with at least 90 per cent by weight of particles having a size below 20 μm, a Radioactive Dentine Abrasion (RDA) determined on an aqueous slurry of the silica powder of 100 to 220, a Pellicle Cleaning Ratio (PCR), when incorporated in a dental composition at 10 per cent by weight, greater than 85, the ratio of PCR to RDA being in the range 0.4:1 to less than 1:1 and having a Plastics Abrasion Value in the range 11 to 19.

2. An amorphous silica according to claim 1 having an oil absorption, using linseed oil, in the range 70 to 150 cm$^3$/100 g.

3. An amorphous silica according to claim 1 having a BET surface area in the range 10 to 450 m$^2$g$^{-1}$.

4. An amorphous silica according to claim 1 having a particle size distribution such that at least 90 per cent by weight of the particles have a size below 17 μm.

5. An amorphous silica according to claim 1 having a weight mean particle size in the range 3 to 7 μm and a particle size distribution such that at least 90 per cent by weight of the particles have a size below 16 μm.

6. An amorphous silica according to claim 1 having a pH value, measured on a 5 per cent by weight suspension, in the range 5 to 8.

7. An amorphous silica according to claim 1 having a water content, as determined by ignition at 1000° C., of up to 25 per cent by weight.

8. An amorphous silica according to claim 1 having a bound water content in the range 3.8 to 5.8 per cent by weight.

9. An amorphous silica according to claim 1 having a loose bulk density in the range 200 to 400 g/dm$^3$.

10. An amorphous silica according to claim 1 having a Pore Volume in the range 0.1 to 1.0 cm$^3$g$^{-1}$.

11. An amorphous silica according to claim 1 having a mean pore diameter in the range 5 to 45 nm.

12. A dental composition comprising an amorphous silica having a weight mean particle size in the range 3 to 15 μm with at least 90 per cent by weight of particles having a size below 20 μm, a Radioactive Dentine Abrasion (RDA) determined on an aqueous slurry of the silica powder of 100 to 220, a Pellicle Cleaning Ratio (PCR) when incorporated in a dental composition at 10 per cent by weight greater than 85, the ratio of PCR to RDA being in the range 0.4:1 to less than 1:1 and having a Plastics Abrasion Value (PAV) in the range 11 to 19 and an orally acceptable carrier.

13. A dental composition according to claim 12 containing from 0.1 to 25 per cent by weight of the amorphous silica.

14. A dental composition according to claim 12 containing from 0.1 to 6 per cent by weight of the amorphous silica.

15. A dental composition according to claim 12 further comprising a second amorphous silica having an RDA value lower than the amorphous silica.

16. A dental composition according to claim 15 containing an amount of amorphous silica in the range 1 to 15 per cent by weight and an amount of a second amorphous silica in the range 4 to 20 per cent by weight.

17. A dental composition according to claim 14 further comprising a principal silica in an amount in the range 4 to 25 per cent by weight.

18. A dental composition according to claim 12 wherein the composition is a clear composition and has a maximum transparency with a light transmission of at least 70 per cent at a refractive index in the range 1.435 to 1.445.

* * * * *